US00PP37627P2

(12) United States Plant Patent
van Swieten

(10) Patent No.: US PP37,627 P2
(45) Date of Patent: Aug. 18, 2026

(54) ***PHALAENOPSIS* PLANT NAMED 'PHA814617'**

(50) Latin Name: *Phalaenopsis hybrida*
Varietal Denomination: PHA814617

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,313

(22) Filed: Sep. 15, 2025

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'PHA814617', characterized by its upright plant habit; moderately vigorous to vigorous growth habit and moderate growth rate; strong flowering stems; freely flowering habit with typically two inflorescences developing per plant, each inflorescence with numerous flowers; medium-sized yellow-colored flowers with reddish-colored labella; and good post-production longevity.

2 Drawing Sheets

Figure 1:
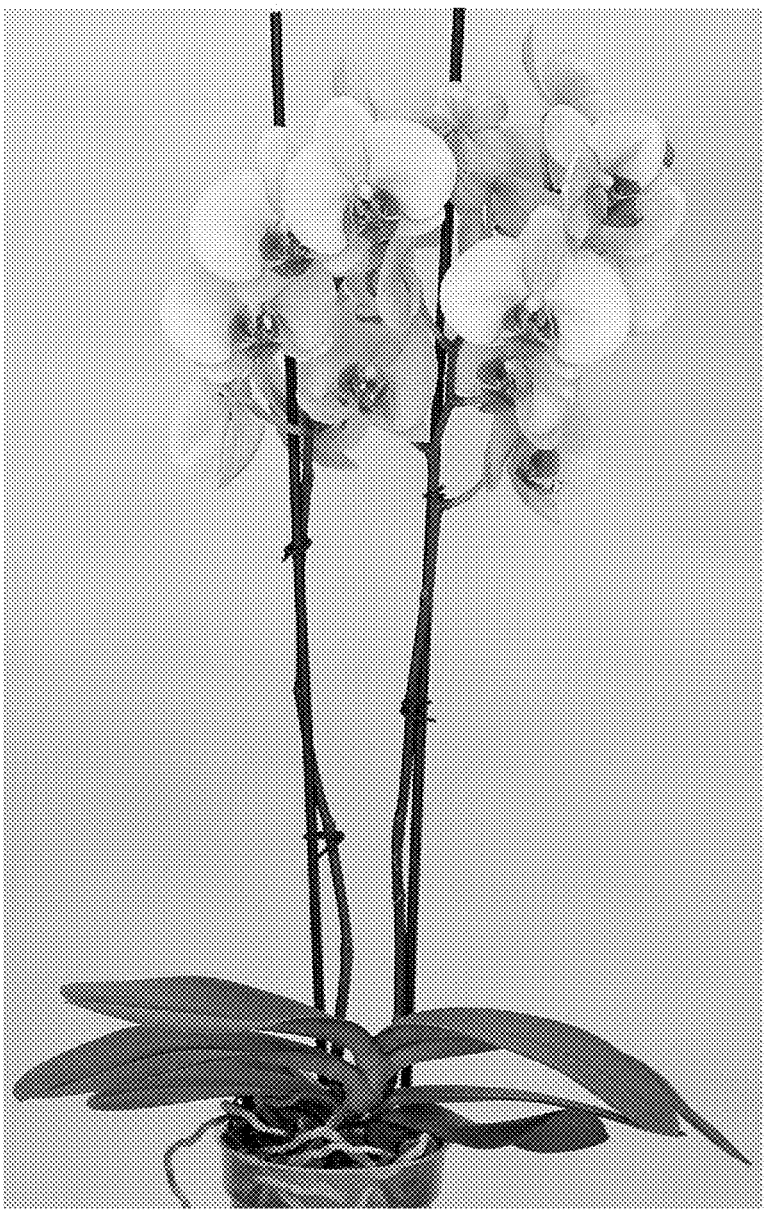

Botanical designation: *Phalaenopsis hybrida.*
Cultivar denomination: 'PHA814617'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1894. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA814617'.

The new *Phalaenopsis* plant is a product of a planned breeding program conducted by the Inventor in Bleiswijk, The Netherlands. The objective of the breeding program is to develop new freely flowering *Phalaenopsis* plants with yellow-colored flowers.

The new *Phalaenopsis* plant originated from a cross-pollination in August, 2017 in Bleiswijk, The Netherlands of a proprietary breeding selection of *Phalaenopsis hybrida* identified as code number 13-056991-0002, not patented, as the female, or seed, parent with a proprietary breeding selection of *Phalaenopsis hybrida* identified as code number 13-057810-0003, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in May, 2020.

Asexual reproduction of the new *Phalaenopsis* plant by in vitro meristem propagation in a controlled environment in Bleiswijk, The Netherlands since May, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA814617'. These characteristics in combination distinguish 'PHA814617' as a new and distinct *Phalaenopsis* plant:

1. Upright plant habit.
2. Moderately vigorous to vigorous growth habit and moderate growth rate.
3. Strong flowering stems.
4. Freely flowering habit with typically two inflorescences developing per plant, each inflorescence with numerous flowers.
5. Medium-sized yellow-colored flowers with reddish-colored labella.
6. Good postproduction longevity.

Plants of the new *Phalaenopsis* can be compared to plants of the female parent selection. Plants of the new *Phalaenopsis* differ primarily from plants of the female parent selection in the following characteristics:

1. Petal margins of plants of the new *Phalaenopsis* are not undulate whereas petal margins of plants of the female parent selection are undulate.

2. The lateral lobes of the labella of plants of the new *Phalaenopsis* are reddish in color whereas the lateral lobes of the labella of plants of the female parent selection are greenish yellow in color.
3. The lateral lobes of the labella of plants of the new *Phalaenopsis* are not as inwardly curved as the lateral lobes of the labella of plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are horizontal in aspect whereas leaves of plants of the male parent selection are semi-erect to horizontal in aspect,
2. The flower column of plants of the new *Phalaenopsis* is yellowish green in color whereas the flower column of plants of the male parent selection is white in color.

Plants of the new *Phalaenopsis* can be compared to plants of *Phalaenopsis hybrida* 'PHA474649', disclosed in U.S. Plant Pat. No. 36,047. In side-by-side comparisons, plants of the new *Phalaenopsis* differ primarily from plants of 'PHA474649' in the following characteristics:

1. Central lobes of the labella of plants of the new *Phalaenopsis* are kite-shaped whereas central lobes of the labella of plants of 'PHA474649' are trullate in shape.
2. Central lobes of the labella of plants of the new *Phalaenopsis* are light red in color whereas central lobes of the labella of plants of 'PHA474649' are purplish red in color.
3. The flower column of plants of the new *Phalaenopsis* is yellowish green in color whereas the flower column of plants of 'PHA474649' is white in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA814617' grown in a container.

Figure 2:
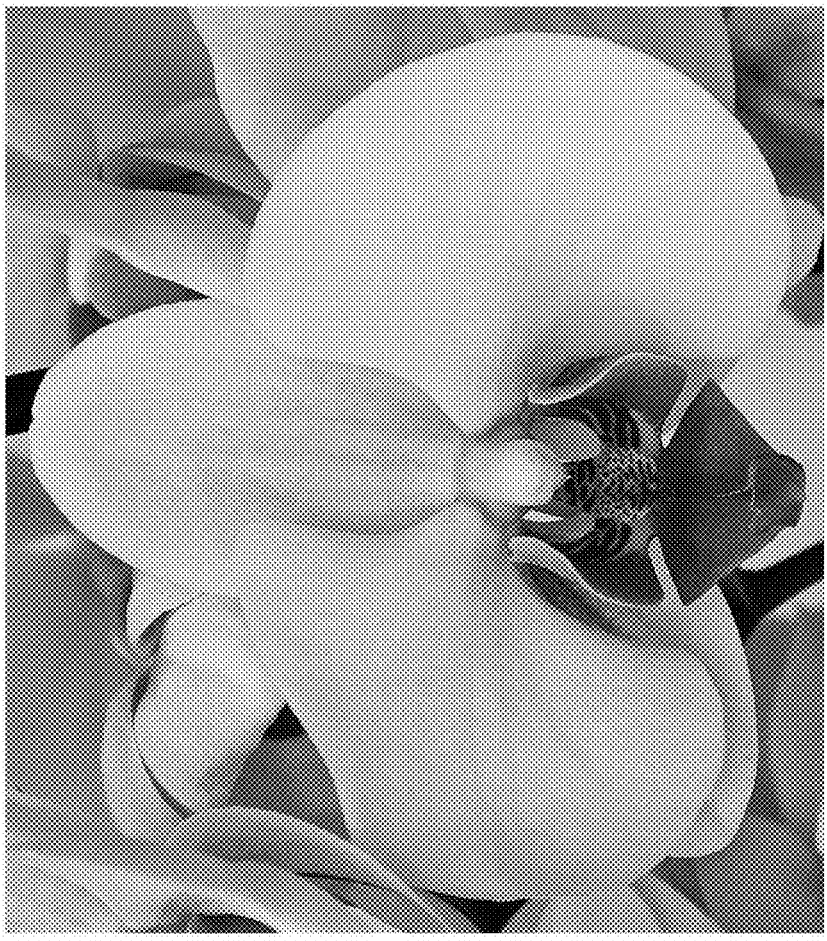

The photograph on the second sheet (FIG. 2) is a close-up view of a typical flower of 'PHA814617'.

DETAILED BOTANICAL DESCRIPTION

The aforementioned photographs and following observations and measurements describe plants grown during the spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA814617'.

Parentage:

*Female, or seed, parent*.—Proprietary breeding selection of *Phalaenopsis hybrida* identified as code number 13-056991-0002, not patented.

*Male, or pollen, parent*.—Proprietary breeding selection of *Phalaenopsis hybrida* identified as code number 13-057810-0003, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit; typically two inflorescences developing per plant, each inflorescence with numerous flowers; monopodial; moderately vigorous to vigorous growth habit and moderate growth rate.

*Plant height, substrate level to top of foliar plane*.—About 14.3 cm.

*Plant height, substrate level to top of floral plane*.—About 50.9 cm.

*Plant diameter or spread*.—About 30.3 cm.

Leaf description:

*Arrangement and quantity*.—Distichous, simple; sessile; about six to seven fully-developed leaves per plant.

*Length*.—About 19.6 cm.

*Width*.—About 6.9 cm.

*Aspect*.—Horizontal.

*Shape*.—Oblanceolate; slightly carinate.

*Apex*.—Unequal obtuse.

*Base*.—Sheathing. Sheath length: About 1.5 cm. Sheath width: About 1.4 cm. Sheath color: Close to a blend of 143C and 144A tinged with close to 197A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to 146A; narrow marginal edges, close to 152B and 152C. Developing leaves, lower surface: Close to 146B variably tinged with close to 200A and 200B. Fully expanded leaves, upper surface: Close to 146A; narrow marginal edges, close to 146C; venation, close to NN137A. Fully expanded leaves, lower surface: Close to 146B; slightly and variably tinged with close to a blend of N186C and 200A; venation, close to 145B slightly tinged with close to a blend of N186C and 200B.

Inflorescence description:

*Appearance and flowering habit*.—Showy zygomorphic flowers arranged on axillary simple or branched racemes; typically two inflorescences develop per plant; each inflorescence with about eleven flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 20 weeks on the plant; flowers not persistent.

*Inflorescence length* (*lowermost flower to inflorescence apex*).—About 24.7 cm.

*Inflorescence width*.—About 16.4 cm.

*Flower buds*.—Height: About 1.9 cm. Diameter: About 1.6 cm by 1.9 cm. Shape: Broadly ovate. Color: Close to a blend of 150B and 151D; towards the base, close to 152D.

*Flower size*.—About 7.9 cm (vertical) by 8.9 cm (horizontal).

*Flower depth*.—About 3 cm.

*Petals, quantity and arrangement*.—Three, two lateral petals and one center petal transformed into a labellum.

*Lateral petals*.—Length: About 4.1 cm. Width: About 5.1 cm. Shape: Reniform to close to broadly lunate. Apex: Rounded. Margin: Entire; not undulate. Texture and luster, upper and lower surfaces: Smooth, glabrous; moderately velvety; matte. Color: When opening, upper surface: Close to 4B to 4C; towards the base, close to 10B; at the base, close to 181C. When opening, lower surface: Close to 3C; towards the base, close to 10A flushed with close to 150C. Fully opened, upper surface: Close to 2D; towards the base, close to 10C tinged with close to 186B and 186C; colors do not change with subsequent development. Fully opened, lower surface: Close to 4C; centers, close to 4B; at the base, close to 186C and 186D; colors do not change with subsequent development.

*Labella*.—Appearance: Three-parted with two lateral lobes and a central lobe; overall shape, broadly cordate to reniform. Length, lateral lobes: About 1.9 cm. Width, lateral lobes: About 1.6 cm. Length, central lobe: About 2.2 cm. Width, central lobe: About 5 mm to 23 mm. Length, cirrhose tips: About 1.5 cm. Shape, lateral lobes: Broadly obovate. Shape, central lobe: Kite-shaped with a slightly elongated apex. Apex, lateral lobes: Obtuse. Apex, central lobe: Minutely acute with two cirrhose apices, pointing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 5.5 mm in length, about 6 mm in width and about 6 mm in height. Color: When opening, upper surface: Lateral lobes: Close to 181C; at the base, close to 4A; narrow marginal edges, close to 11B. Central lobe: Close to 180D; towards the base, tinged with close to 174B; at the base, close to 3B and 186A with radial stripes, close to 186A; main vein, close to 180C; cirrhose apices, close to 175A and distally, close to 10D. Callosities: Close to 12A and 12B; towards the apex, fine dots and stripes, close to 181A. When opening, lower surface: Lateral lobes: Close to 164A and 164B; lower third, close to 154B and 154C; narrow marginal edges, close to 11B. Central lobe: Close to 174B; centers, close to N144A and N144B; at the base, close to N144B and 181A; main vein, close to 144A; cirrhose apices, close to 175A, distally, close to 10D. Fully opened, upper surface: Lateral lobes: Close to 181C; towards the apex and margins, close to 164C and 164D; at the base, axial stripes, close to 5A; narrow marginal edges, close to 11B. Central lobe: Close to 181D; towards the base, tinged with close to 163C; at the base, close to 3A and N186D with radial stripes, close to a blend of 46A and 181A; main vein, close to 181C; cirrhose apices, close to 175A and distally, close to 10D. Callosities: Close to 12A; towards the apex, close to 13A; fine dots and stripes, close to 46A. Fully opened, lower surface: Lateral lobes: Close to 164B; lower third, close to 154B; narrow marginal edges, close to 11B. Central lobe: Close to 174B; centers, close to 145B; at the base, close to 153D and 187B; main vein, close to 145A; cirrhose apices, close to 175A, distally, close to 10D.

*Sepals*.—Quantity and arrangement: Three, one upper dorsal sepal and two lower lateral sepals. Length, dorsal sepal: About 4.4 cm. Width, dorsal sepal: About 2.8 cm. Length, lateral sepals: About 4.4 cm. Width, lateral sepals: About 2.7 cm. Shape, dorsal sepal: Elliptic to ovate-elliptic. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 2C; towards the apex and margins, close to 4B; at the base, tinged with close to 174D. When opening, lower surface: Close to a blend of 1B and 154B; towards the apex and margins, close to 154C; towards the base, close to 151C and 151D. Fully opened, upper surface: Close to 6D; towards the apex and margins, close to 5D; at the base, tinged with close to 182C. Fully opened, lower surface: Close to 8B; towards the apex and margins, close to 6D; towards the base, close to 1C. Color, lateral sepals: When opening, upper surface: Close to a blend of 1B and 2B; towards the base, close to 154B with fine dots, close to 174B. When opening, lower surface: Close to 151C and 151D; main vein, close to N144A. Fully opened, upper surface: Close to 3C; towards the margins, close to 4C; towards the base, fine dots, close to 182B and 182C. Fully opened, lower surface: Close to 3C; main vein, close to N144B.

*Peduncles*.—Length: About 49.2 cm. Diameter: About 6 mm. Strength: Strong. Aspect: Upright to outwardly arching. Texture and luster: Smooth, glabrous; matte. Color: Close to a blend of 147A and 197A; densely covered with fine dots, close to 147C.

*Pedicels*.—Length: About 4.6 cm. Diameter: About 3.5 mm. Strength: Moderately strong. Aspect: About 55° from peduncle axis. Texture and luster: Smooth, glabrous; matte. Color: Close to 145B; proximal end, close to 145A tinged with close to N199B.

*Reproductive organs*.—Androecium: Column length: About 8 mm. Column width: About 6 mm. Column color: Close to 145D. Pollinia quantity: Two. Pollinia diameter (per two pollinia): About 2.5 mm. Pollinia color: Close to 23A. Gynoecium: Stigma length: About 3 mm. Stigma width: About 5 mm. Stigma shape: Reniform. Stigma color: Close to 145D. Ovary length: About 1 cm. Ovary diameter: About 1 mm. Ovary color: Close to 145C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA814617' as herein illustrated and described.

* * * * *